United States Patent [19]

Villa et al.

[11] Patent Number: 5,362,905
[45] Date of Patent: Nov. 8, 1994

[54] PROCESS FOR THE PREPARATION OF L-5-(2-ACETOXY-PROPIONYLAMINO)-2,4,6-TRIIODO-ISOPHTHALIC ACID DICHLORIDE

[75] Inventors: Marco Villa; Maurizio Paiocchi, both of Milan; Aldo Di Caterino, Sesto San Giovanni Milan, all of Italy

[73] Assignee: Zambon Group S.p.A., Vicenza, Italy

[21] Appl. No.: 139,802

[22] Filed: Oct. 22, 1993

[30] Foreign Application Priority Data

Oct. 27, 1992 [IT] Italy .................. MI92 A 002450

[51] Int. Cl.⁵ .................. C07C 67/02; C07B 43/06
[52] U.S. Cl. .................. 560/250; 560/252
[58] Field of Search .................. 560/250 252

[56] References Cited

U.S. PATENT DOCUMENTS 4,139,605 2/1979 Felder et al. .................. 424/1.85
4,364,921 12/1982 Speck et al. .................. 424/5
4,547,357 10/1985 Pfeiffer et al. .................. 424/5

FOREIGN PATENT DOCUMENTS 1472050 4/1977 United Kingdom .

OTHER PUBLICATIONS

March, J., Advanced Organic Chemistry: Reactions, Mechanisms, and Structure, III Ed., 1985, pp. 227–229, & 481.

*Primary Examiner*—Arthur C. Prescott
*Attorney, Agent, or Firm*—Oblon, Spivak, McClelland, Maier & Neustadt

[57] ABSTRACT

An improvement to a process for the preparation of L-5-(2-acetoxy-propionylamino)-2,4,6-triiodo-isophthalic acid dichloride by reacting 5-amino-2,4,6-triiodo-isophthalic acid dichloride with L-2-acetoxy-propionyl-chloride, is described.

4 Claims, No Drawings

PROCESS FOR THE PREPARATION OF L-5-(2-ACETOXY-PROPIONYLAMINO)-2,4,6-TRIIODO-ISOPHTHALIC ACID DICHLORIDE

The present invention relates to a process for the preparation of an intermediate of the organic synthesis and more particularly relates to a process for the preparation of L-5-(2-acetoxy-propionylamino)-2,4,6-triiodo-isophthalic acid dichloride (from now on indicated as compound A).

The compound A, described for the first time by the Swiss Company Savac AG, for instance in the British patent No. 1,472,050, can be used as an intermediate in the synthesis of the compound L-5-(2-hydroxypropionylamino)-2,4,6-triiodo-isophthalic acid bis-(1,3-dihydroxypropylamide), also described in the same British patent above cited, which in turn can be used in diagnostics as a non-ionic X-rays contrast media.

To our knowledge, the industrial synthesis of compound A still is the one described in the aforesaid British patent and consists of the following steps:

1. the starting material, 5-amino-2,4,6-triiodo-isophthalic acid (compound B), is prepared by iodination of 5-amino-isophthalic acid;
2. preparation of 5-amino-2,4,6-triiodo-isophthalic acid dichloride (compound C);
3. reaction of compound C with the chloride of L-2-acetoxy-propionic acid (acetyl-lactic acid) to give L-5-(2-acetoxy-propionylamino)-2,4,6-triiodo-isophthalic acid dichloride (compound A).

The reaction of step 3 has been described in example 1 point B of the British patent above mentioned.

Said reaction is carried out by adding L-2-acetoxy-propionyl-chloride to a solution of 5-amino-2,4,6-triiodo-isophthalic acid dichloride in dimethylacetamide at 3°–5° C.

The equivalents ratio between 5-amino-2,4,6-triiodo-isophthalic acid dichloride (compound C) and 2-acetoxy-propionyl-chloride is 1:2.5. The work-up of the reaction mixture, described in example 1-B of the British patent No. 1,472,050, comprises the evaporation of the dimethylacetamide (from now on indicated as DMA) and the suspension of the oily residue in water and ice.

A crude precipitate is obtained (98% yield), which is purified by suspension in chloroform.

The repetition of the above described reaction in our Laboratories afforded the product with 50% yield (based on the HPLC titre of the crude product); the work-up of the reaction evidenced remarkable drawbacks since it foresees the concentration of the solvent under vacuum and such an industrial operation needs several hours because dimethylacetamide (DMA) is a high boiling solvent (165° C.).

By carrying out the reaction as described in the British patent a crude product is therefore obtained consisting of a 50:50 mixture of starting material and compound A and other impurities (up to 10%) mainly constituted by hydrolysis products of the chlorocarbonyl groups.

Therefore the reaction was repeated at higher temperatures in order to bring the conversion at higher levels but also in these conditions it was not possible to complete the reaction.

Now we have surprisingly found that by carrying out the reaction in the presence of a Lewis acid, the desired product A is obtained in high yields and practically quantitative conversion and, in the meantime, it is possible to vary the solvent avoiding the above cited drawbacks in the work-up of the reaction mixture.

Therefore it is the object of the present invention, in a process for the preparation of L-5-(2-acetoxy-propionylamino)-2,4,6-triiodo-isophthalic acid dichloride by reacting 5-amino-2,4,6-triiodo-isophthalic acid dichloride with L-2-acetoxy-propionyl-chloride, the improvement consisting in operating in the presence of a Lewis acid.

By the term Lewis acid we refer to a salt of a transitional metal having Lewis acid characteristics (see J. March, Advanced Organic Chemistry, III Ed., pages 227–229, for a definition) and, in particular, we refer to salts of metals which are "hard" and "border line" Lewis acids (see the reference above cited at page 229) with a preference for these latter.

Preferred examples are zinc chloride, aluminum chloride and stannous chloride.

The use of a Lewis acid in a reaction wherein one of the reagents contains an amino group, compound C is 5-amino-isophthalic acid dichloride, is normally considered a chemical non-sense because the high reactivity of Lewis acids towards the amino groups is well known (see J. March, Advanced Organic Chemistry, III Ed., page. 481).

It is therefore surprising that the reaction between compound C and 2-acetoxy-propionyl-chloride can be carried out in the presence of a Lewis acid giving the desired amidation product with high yields. A relevant aspect of the invention is constituted by the fact that the Lewis acid can be used in catalytic amounts comprised for instance between 0.1 and 10% in mols with respect to the substrate. Higher amounts of Lewis acid are equally effective but useless. Moreover, in the reaction object of the present invention, the molar ratio between compound C and 2-acetoxy-propionyl-chloride may be lowered to 1:1.5 with evident economic advantages.

As previously said, the reaction solvent may be other than DMA with advantages in the work-up of the reaction mixture. Suitable solvents are methylene chloride, toluene, 1,2-dichloroethane.

In a preferred embodiment, the process object of the invention is carried out according to the following operating conditions. 2-acetoxy-propionyl-chloride is added at room temperature to a mixture of compound C and Lewis acid in methylene chloride. The reaction mixture is heated and the progress of the reaction is monitored.

Once the desired degree of conversion is reached (even 100%), the mixture is processed in order to eliminate the Lewis acid and the solvent.

The resultant crude product is constituted by compound A with yields higher than 90% and with a purity sufficient to use it in the subsequent steps of the process for the preparation of L-5-(2-hydroxy-propionylamino)-2,4,6-triiodo-isophthalic acid bis-(1,3-dihydroxy-propionylamide), without further purifications.

With the aim to better illustrate the present invention, without limiting it, the following examples are now given.

EXAMPLE 1

Zinc chloride (0.53 g; 3.87 mmols) was added to a mixture of 5-amino-2,4,6-triiodo-isophthalic acid dichloride (25 g; 28.7 mmols; 92.3% HPLC titre) in methylene chloride (150 ml) kept at 20° C. and L-2-acetoxypropionyl-chloride (8.75 g; 58.1 mmols) was added dropwise in about 10 minutes.

The mixture was refluxed for 12 hours. The reaction was monitored by thin-layer chromatography (TLC) (silica gel, eluent ethyl ether:hexane=8:2).

At the end of the reaction, the mixture was cooled at room temperature, and poured into 2N hydrochloric acid (100 ml) and methylene chloride (100 ml).

The phases were separated and the organic phase was washed twice with water (100 ml), dried on sodium sulfate and finally evaporated to dryness under vacuum.

26.2 g of crude product, that on a base of HPLC analysis contained L-5-(2-acetoxy-propionylamino)-2,4,6-triiodo-isophthalic acid dichloride, were obtained (24.9 g; 35.1 mmols; 90.6% yield) m.p. 221°–223° C. (toluene). The crude product was used as such in the subsequent steps of the process according to the British patent No. 1,472,050.

EXAMPLE 2

Zinc chloride (0.027 g; 0.2 mmols) was added to a mixture of 5-amino-2,4,6-triiodo-isophthalic acid dichloride (1.22 g; 2 mmols; 97.5% HPLC titre) in toluene (7.5 ml) kept at 20° C. and L-2-acetoxy-propionyl-chloride (0.45 g; 3 mmols) was added dropwise in about 10 minutes.

The mixture was refluxed for 24 hours. The reaction was monitored by thin-layer chromatography (TLC) (silica gel, eluent ethyl ether:hexane=8:2).

At the end of the reaction, the mixture was cooled at room temperature, and poured into 2N hydrochloric acid (10 ml) and methylene chloride (10 ml).

The phases were separated and the organic phase was washed twice with water (10 ml), dried on sodium sulfate and evaporated to dryness under vacuum.

1.4 g of crude product that on a base of HPLC analysis contained L-5-(2-acetoxy-propionylamino)-2,4,6-triiodo-isophthalic acid dichloride (1.28 g; 1.8 mmols; 90.0% yield) were obtained.

EXAMPLE 3

Stannous chloride (0.038 g; 0.2 mmols) was added to a mixture of 5-amino-2,4,6-triiodo-isophthalic acid dichloride (1.22 g; 2 mmols; 97.5% HPLC titre) in methylene chloride (7.5 ml) kept at 20° C. and L-2-acetoxy-propionyl-chloride (0.45 g; 3 mmols) was added dropwise in about 10 minutes.

The mixture was refluxed for 3 hours. The reaction was monitored by thin-layer chromatography (TLC) (silica gel, eluent ethyl ether:hexane=8:2).

At the end of the reaction, the mixture was cooled at room temperature, and poured into 2N hydrochloric acid (10 ml) and methylene chloride (10 ml).

The phases were separated and the organic phase was washed twice with water (10 ml), filtered over celite, dried on sodium sulfate and finally evaporated to dryness under vacuum.

1.4 g of crude product that on a base of HPLC analysis contained L-5-(2-acetoxy-propionylamino)-2,4,6-triiodo-isophthalic acid dichloride (1.24 g; 1.75 mmols; 87.5% yield) were obtained.

EXAMPLE 4

Aluminum chloride (0.027 g; 0.2 mmols) was added to a mixture of 5-amino-2,4,6-triiodo-isophthalic acid dichloride (1.22 g; 1.4 mmols; 97.5% HPLC titre) in methylene chloride (7.5 ml) kept at 20° C. and L-2-acetoxy-propionyl-chloride (0.45 g; 3 mmols) was added dropwise in about 10 minutes.

The mixture was refluxed for 24 hours. The reaction was monitored by thin-layer chromatography (TLC) (silica gel, eluent ethyl ether:hexane=8:2).

The mixture was cooled at room temperature, and poured into 2N hydrochloric acid (10 ml) and methylene chloride (10 ml).

The phases were separated. The organic phase was washed twice with water (10 ml), filtered over celite, dried on sodium sulfate and evaporated to dryness under vacuum. 1.5 g of crude product that on a base of HPLC analysis contained L-5-(2-acetoxy-propionylamino)-2,4,6-triiodo-isophthalic acid dichloride (0.74 g; 1.04 mmols; 52% yield) and 5-amino-2,4,6-triiodo-isophthalic acid dichloride (0.58 g; 0.84 mmols) were obtained.

What we claim is:

1. In a process for the preparation of L-5-(2-acetoxy-propionylamino)-2,4,6-triiodo-isophthalic acid dichloride by reacting 5-amino-2,4,6-triiodo-isophthalic acid dichloride with L-2-acetoxy-propionyl-chloride, the improvement consisting in operating in the presence of a Lewis acid.

2. A process according to claim 1 wherein the Lewis acid is used in catalytic amounts.

3. A process according to claim 1 or 2 wherein the Lewis acid is a "border line" acid.

4. A process according to claim 1 or 2 wherein the Lewis acid is selected from the group consisting of zinc chloride, aluminum chloride and stannous chloride.

* * * * *